(12) United States Patent
Singh et al.

(10) Patent No.: US 9,931,309 B2
(45) Date of Patent: Apr. 3, 2018

(54) CURCUMIN-SOPHOROLIPID COMPLEX

(71) Applicant: COUNCIL OF SCIENTIFIC & INDUSTRIAL RESEARCH, New Delhi (IN)

(72) Inventors: Pradeep Kumar Singh, Pune (IN); Asmita Ashutosh Prabhune, Pune (IN); Satishchandra Balkrishna Ogale, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/328,304

(22) PCT Filed: Jul. 23, 2015

(86) PCT No.: PCT/IN2015/000296
§ 371 (c)(1),
(2) Date: Jan. 23, 2017

(87) PCT Pub. No.: WO2016/013026
PCT Pub. Date: Jan. 28, 2016

(65) Prior Publication Data
US 2017/0224636 A1 Aug. 10, 2017

(30) Foreign Application Priority Data
Jul. 23, 2014 (IN) .......................... 2076/DEL/2014

(51) Int. Cl.
*A61K 31/12* (2006.01)
*A61K 9/20* (2006.01)
*A61K 45/06* (2006.01)
*A61K 47/48* (2006.01)

(52) U.S. Cl.
CPC ............... *A61K 31/12* (2013.01); *A61K 9/20* (2013.01); *A61K 45/06* (2013.01); *A61K 47/48046* (2013.01)

(58) Field of Classification Search
CPC .................................................... A61K 31/12
See application file for complete search history.

(56) References Cited

FOREIGN PATENT DOCUMENTS

JP 2003-253105 9/2003

OTHER PUBLICATIONS

Barik et al., "Photophysical Studies on Binding of Curcumin to Bovine Serum Albumin" *Photochem and Photobio*, 2003; 77(6): 597-603.
Began et al., "Interaction of Curcumin with Phosphatidylcholine: A Spectrofluorometric Study" *J. Agric. Food Chem.*, 1999; 47: 4992-97.
International Search Report and Written Opinion issued in Application No. PCT/IN2015/000296, dated Nov. 23, 2015.
Patra et al., "Effect of Curcumin on Liposome: Curcumin as a Molecular Probe for Monitoring Interaction of Ionic Liquids with 1,2-Dipalmitoyl-sn-Glycero-3-Phosphocholine Liposome" *Photochem and Photobio*, 2012; 88(2):: 319.
Pradeep Kumar Singh et al., "Correction: from micron to nano-curcumin by sophorolipid co-processing: highly enhanced bioavailability, fluorescence, and anti-cancer efficacy." *RSC Advances: An International Journal to Further the Chemical Sciences*, 2015; 5(28): 2046-2069.
Pradeep Kumar Singh et al., "From micron to nano-curcumin by sophorolipid co-processing: highly enhances bioavailability, fluorescence, and anti-cancer efficacy," *RSC Adv.*, 2014; 4(4): 60334-60341.
Singh, P. and S. S. Cameotra, "Potential applications of microbial surfactants in biomedical sciences" *TRENDS in Biotechnology*, 2004; 22(3): 142.
XP002750784, *Thomson Scientific*, Week 200419, abstract of Japanese Patent Application No. 2003-253105 published Sep. 10, 2003.
Yu, Hailong and Qingrong Huang, "Improving the Oral Bioavailability of Curcumin Using Novel Organogel-Based Nanoemulsions" *J. Agric. Food Chem.*, 2012; 60(21): 5373-79.

*Primary Examiner* — Sahar Javanmard
(74) *Attorney, Agent, or Firm* — Norton Rose Fulbright US LLP

(57) ABSTRACT

The present invention relates to a complex comprising acidic sophorolipid and curcumin ((SL(A)+Cur), wherein, curcumin is solubilized and nano-encapsulated in acidic sophorolipid to improve the water solubility, stability and bioavailability of curcumin in order to enhance its therapeutic activity. Further, the invention provides pharmaceutical compositions comprising the present complex and methods to treat cancer in a subject using the said composition.

15 Claims, 15 Drawing Sheets

☐ SL: Sophorolipids
▨ C-SL: Curcumin Sophorolipids
▬ Cur: Curcumin

CURCUMIN-SOPHOROLIPID COMPLEX

CROSS-REFERENCE TO RELATED APPLICATIONS

This application is a national phase application under 35 U.S.C. § 371 of International Application No. PCT/IN2015/000296 filed 23 Jul. 2015, which claims priority to Indian Patent Application No. 2076/DEL/2014 filed 23 Jul. 2014. The entire contents of each of the above-referenced disclosures is specifically incorporated herein by reference without disclaimer.

FIELD OF THE INVENTION

The present invention relates to a curcumin-acidic sophorolipid complex wherein the bioavailability of curcumin is enhanced. Particularly, the present invention relates to composition comprising curcumin and acidic sophorolipid wherein curcumin is solubilized and nano-encapsulated in acidic sophorolipid.

More particularly, present invention relates to an economically feasible process for the preparation of acidic curcumin-sophorolipid complex.

Additionally, the present invention relates to use of the curcumin-sophorolipid complex in treatment of cancer, specifically breast cancer.

BACKGROUND OF THE INVENTION

Curcumin (Cur) is a principal curcuminoid of *Curcuma longa*, a member of the Zingiberaceae family. The plant is distributed throughout tropical and subtropical regions of the world, being widely cultivated in south and south-east Asian countries. Turmeric, i.e., the ground rhizomes of *C. longa* has been long used in food as a spice, and as a main colouring substance. Curcumin possesses several health endowing properties vis-a-vis, antioxidant, anti-inflammatory, anti-carcinogenic, chemo-preventive, anti-microbial and chemo-therapeutic properties. The manifold benefits of curcumin, however, are restricted by its low oral bioavailability, indicated by the rate and extent at which orally administered curcumin enters the systemic circulation and reaches target sites.

The vital factors influencing the bioavailability of a therapeutic molecule are solubilization, absorption, and metabolism. It is a known fact that curcumin is insoluble in aqueous solutions and requires a solvent system for its complete dissolution. Internally curcumin undergoes rapid metabolism in the human body therefore rendering the absorption rate of curcumin to remain elusive. A major portion of this compound remains unabsorbed due to a fairly low intestinal absorption capacity. Even the minor amount which is actually absorbed is rapidly metabolized in the liver and eliminated from the body by the gall bladder. Various studies have verified that even a very high oral dose of curcumin i.e. up to 1 $g/kg^{-1}$ of the body weight is almost completely eliminated by the human metabolic system. In view of the limiting factors affecting the oral bioavailability of curcumin, it is necessary to devise mechanisms of solubilization and absorption, appropriate for developing formulations which are able to improve the solubilization and the oral bioavailability of curcumin.

Curcumin i.e. diferuloylmethane, a bright orange yellow pigment is the main active ingredient of turmeric. Curcumin exhibits tautomerism in its molecular structure and thus exists in the enol form in nonpolar solvents, because of intra-molecular hydrogen bond formation and in the di-keto form in polar solvents. The keto form of Curcumin acts as a proton donor in acidic and neutral media, whereas at pH values above 8 the enol form dominates and acts as an electron donor. The existence of the phenolic, beta-diketone, as well as the methoxy groups of Curcumin contribute to its free-radical scavenging property. This property imparts the anti-cancer character to this compound. However, these results have not been reflected well in clinical studies mainly due to the low oral bioavailability of Curcumin. Therefore, several soft material systems including liposomes, microspheres, dendrimers, micelles, hydrogels and solid lipid nanoscale particles have been explored to design specific drug-delivery systems for curcumin. These nano-assembly forming procedures designed to improve the bio-availability of curcumin are all inherently expensive and hence there is a strong urge to obtain cost-effective replacements for this system.

There are a few research studies that emphasize the use of nanotechnology based methods to enhance bioavailability of insoluble therapeutic molecules, one of them being curcumin. Hailong Yu and Qingrong Huang in J. Agric. Food Chem., 2012, 60 (21), 5373-79 discloses organogel-based nanoemulsions developed for oral delivery of curcumin and improvement of its bioavailability. The surfactant employed for the dissolution of curcumin therein was Tween 20, the solvent being known for its role in development and reproductive toxicity in animal studies. Also there have also been concerns raised of contamination of Tween 20 or polysorbate 20 with carcinogenic 1,4-dioxane. Therefore, the use of biocompatible environmentally friendly ingredients having absolutely no hazardous effects on human beings may be used in the development of nano-emulsion or micro-emulsion based formulations comprising curcumin.

Biosurfactants derived from microorganisms are an interesting category of bio-organic systems with potential applications in biomedical science. They can be produced from renewable feedstock or waste material by natural fermentation. These amphiphilic compounds are known to easily form self assemblies at different pH conditions in aqueous environment. Sophorolipids are an eco-friendly and biocompatible class of amphiphilic biosurfactants which easily form emulsions in aqueous solution to reduce the surface tension and interfacial energies. Sophorolipids possess unique structures that can be engineered to suit specific application domains. Sophorolipid exists in two forms—acidic and lactonic. Lactonic sophorolipids have revealed superior anti-microbial, antiviral, antifungal, anti-inflammatory and anti-cancer activity. In present invention we have applied acidic sophorolipid to enhanced curcumin solubility, bioavailability and as a carrier in drug delivery to treat cancer cell line. Acidic sophorolipids (SL(A)), are known to form micelles, which interact depending on the pH of the system. SL(A), is composed of a sophorose unit attached to an oleic acid moiety through an ether bond on the C17 carbon atom of the fatty acid chain. This particular characteristic leaves the —COOH group available and responsive to changes in pH of the solution giving rise to the possibility of a series of self-assembled structures.

In the light of the prior arts with regard to available expensive technologies in preparing various nano-systems in improving the bioavailability of curcumin, there is still a scope in the art to provide cost-effective and bioavailable curcumin compositions.

OBJECTS OF THE INVENTION

Main object of the present invention is to provide acidic curcumin-sophorolipid complex[SL(A)+Cur], the said curcumin component having enhanced bioavailability.

Another object of the present invention is to devise an economically feasible process via green nano-technology to provide the present SL(A)+Curcomplex.

Yet another object of the present invention is to provide a cost-effective pharmaceutical composition comprising the present nano-self-assembled complex for improved curcumin delivery and efficacy in chemo-therapeutic treatment.

Still another object of the present invention is to provide a pharmaceutical composition comprising curcumin-sophorolipid complex for treatment of cancer, specifically breast cancer.

SUMMARY OF THE INVENTION

Accordingly, the present invention provides a curcumin-sophorolipid complex comprising acidic sophorolipid and curcumin in a ratio ranging from 6:1 to 1:1 (w/v).

In another embodiment, present invention provides a complex wherein curcumin is solubilized and encapsulated in acidic sophorolipid to improve the solubility, stability and bioavailability of curcumin.

In another embodiment of the present invention, said complex comprises sophorolipid and curcumin in a ratio of 5:1.

In yet another embodiment of the present invention, the complex has a particle size ranging from 5 to 30 nm.

In still another embodiment of the present invention, said complex is in aqueous form.

In yet another embodiment of the present invention, there is provided a complex for treatment of breast cancer.

In another embodiment of the present invention, there is provided a complex for use in preparation of medicament for treatment of breast cancer.

In yet another embodiment, present invention provides a process for the preparation of curcumin-sophorolipid complex comprising the steps of:
  (i) sonicating 80 to 90 (wt %) sophorolipid solution for a period ranging from 15 to 30 minutes with addition of 10 to 20 (wt %) curcumin solution at a rate of 0.5 ml/min to obtain a solution;
  (ii) drying the solution of step (i) followed by addition of water for complete dispersion of curcumin to achieve a uniform dispersion; and
  (iii) filtering the uniform dispersion of step (ii) to obtain the curcumin-sophorolipid complex.

In still another embodiment, present invention provides a pharmaceutical composition comprising curcumin-sophorolipid complex and a pharmaceutically acceptable excipient, wherein curcumin-sophorolipid complex ranges from 0.001 to 99.99% of total weight of the pharmaceutical composition.

Another embodiment of the present invention provides a pharmaceutical composition comprising an agent having anti-oxidant, anti-cancer, or anti-adipogenic activity In yet another embodiment of the present invention, the excipient is selected from the group consisting of tableting excipients, injectable excipients, and excipients.

In another embodiment of the present invention, the composition is formulated as a tablet, capsule, pellet, granule, oral powder, injectable powder, syrup, solution, liquid ampoule, dispersion, aerosol spray, semi-solid, softgel, aerosol, or suspensions including nano and micro suspensions.

In yet another embodiment of the present invention, the agent is selected from the group consisting of rituximab, bevacizumab, imatinib, leuprorelin, lenalido-midecetuximab, and trastuzumab.

In yet another embodiment the present invention provides a method of treating cancer in a subject, wherein the method comprises administering to a subject a therapeutically effective amount of the pharmaceutical composition comprising acidic sophorolipid and curcumin complex and one or more pharmaceutically acceptable excipients.

In yet another embodiment the present invention provides a method of treating cancer in a subject, wherein the method comprises administering to a subject a therapeutically effective amount of the pharmaceutical composition comprising acidic sophorolipid and curcumin complex, one or more pharmaceutically acceptable excipients, and optionally one or more agents having anti-oxidant, anti-cancer, oranti-adipogenic activity.

In yet another embodiment the present invention provides a cost-effective process for preparation of acidic sophorolipid and curcumin complex, wherein the acidic sophorolipid and curcumin complex is prepared by sonication driven supramolecular self-assembly.

BRIEF DESCRIPTION OF ACCOMPANYING DRAWINGS

FIG. 1 relates to the optical properties i.e. UV-Visible spectra measurement and photoluminescence attributes of SL(A), Curcumin and the present complex of SL(A)+Cur solution. FIG. 1(a) depicts UV-vis spectra of SL(A) solution having absorbance at $\lambda=234$ nm, Curcumin solution having absorbance at $\lambda=344$ and 420 nm while SL(A)+Cur shows a distinct peak with an increase in absorption at 420 nm. FIG. 1(b) depicts the photoluminescence properties of SL(A) solution which fails to exhibit any photoluminescence, Curcumin solution exhibits photoluminescence at 550 nm while the present SL(A)+Cur complex shows very strong photoluminescence at 496 nm. FIG. 1(c) depicts photo luminescence quenching and right shift of SL(A)+Cur self-assembly on gradually addition of ethanol solvent; and FIG. 1(d) depicts photoluminescence quenching of SL(A)+Cur mixture in ethanol on gradually addition of water.

FIG. 2 depicts optical microscopy and fluorescence images of Cur and SL(A)+Cur self-assembly, wherein FIG. 2(a) depicts curcumin solution in white light and FIG. 2(c) depicts the present SL(A)+Cur self-assembly in white light. Further, FIG. 2(b) depicts curcumin solution in green light and FIG. 2(d) depicts the present SL(A)+Cur self-assembly in green filter (scale bar 100 μm).

Figure 6:
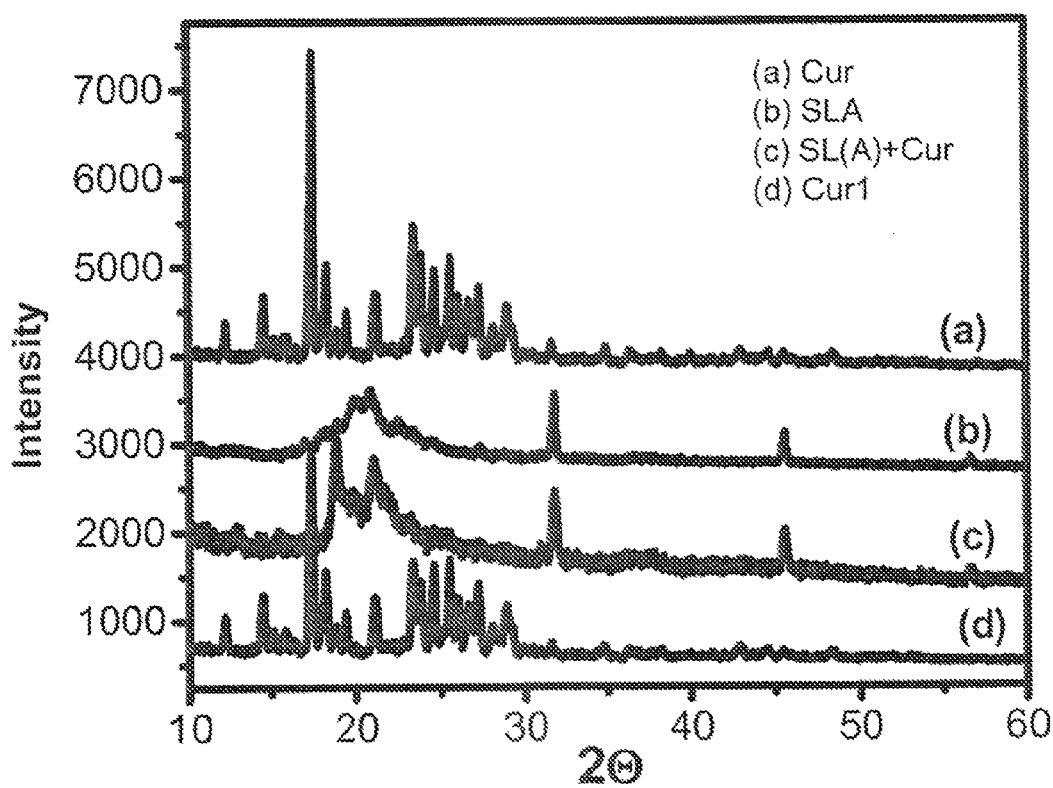
Figure 7:
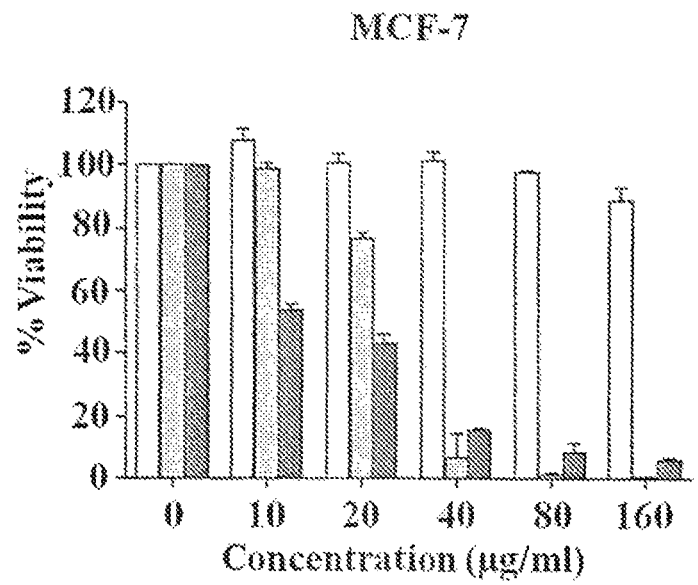
Figure 7:
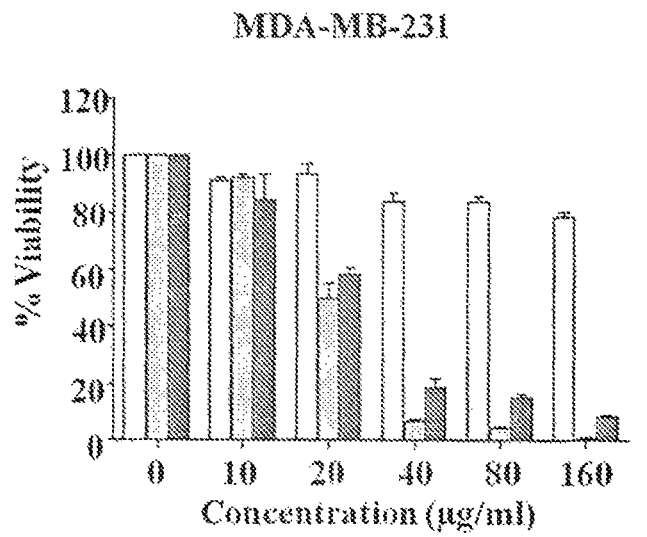

FIG. 6 depicts XRD spectra of SL(A)+Cur self assembly. Line (a) explain the Cur XRD pattern, (b) SL(A), (c) SL(A)+Cur (d) SL(A)+Cur after dissolve in chloroform solvent. (d) line showed unaffected nature of curcumin encapsulated in SL(A) self assembly FIG. 7 depicts cytotoxicity analysis of Sophorolipids (SL), Curcumin-sophorolipid (C-SL) and Curcumin (Cur) by MTT assay in MCF-7 and MDA-MB-231 cells. All the data are presented as mean±SD of five independent experiments at p<0.0001, indicating statistically significant differences compared to the control untreated group.

Figure 8:
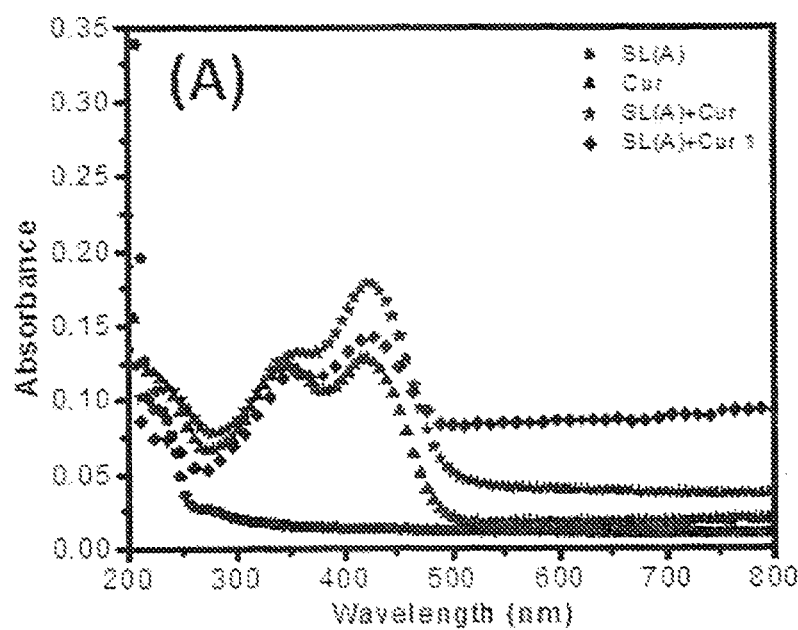
Figure 8:
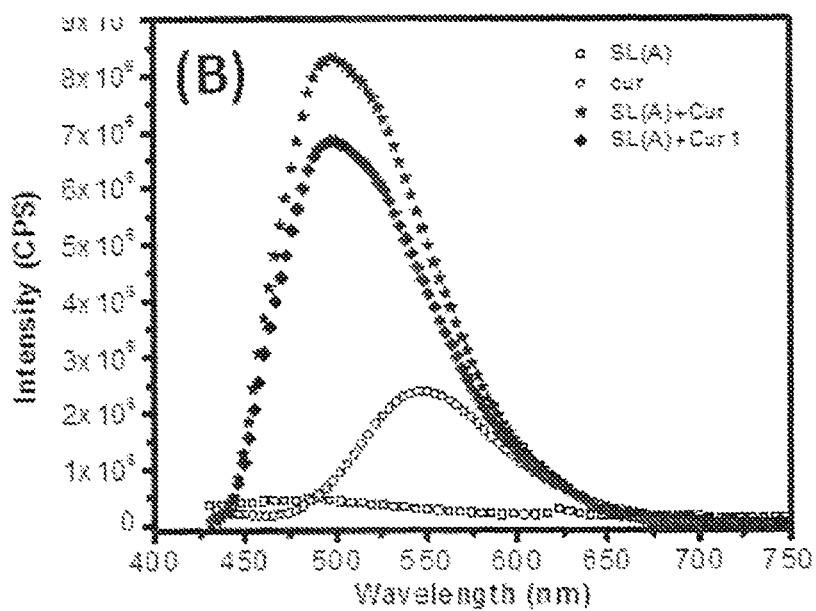

FIG. 8 The stability of the nano-complex in aqueous environment over a period of four months was confirmed by UV/Vis spectra and photoluminescence. UV-Visible spectra of SL (A), Curcumin and SL(A)+ Cur solutions. SL(A) solution shows absorbance at λ=234 nm and Curcumin solution at λ=344 and 420 nm while SL(A)+Cur showing increase absorption at one peak at 420 nm. Cubical shape line shows the stability of nano complex after four months.

Figure 9:
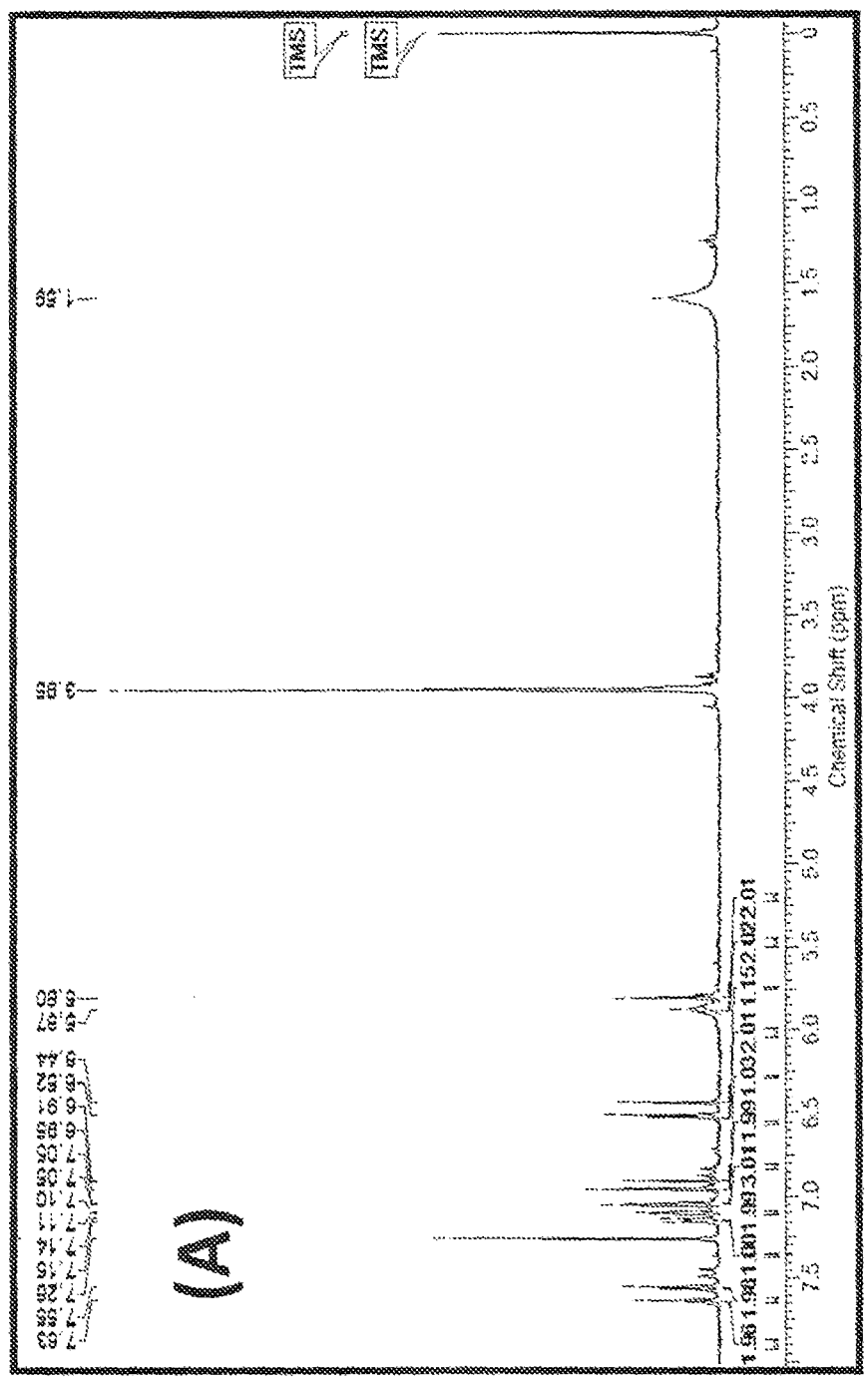
Figure 9:
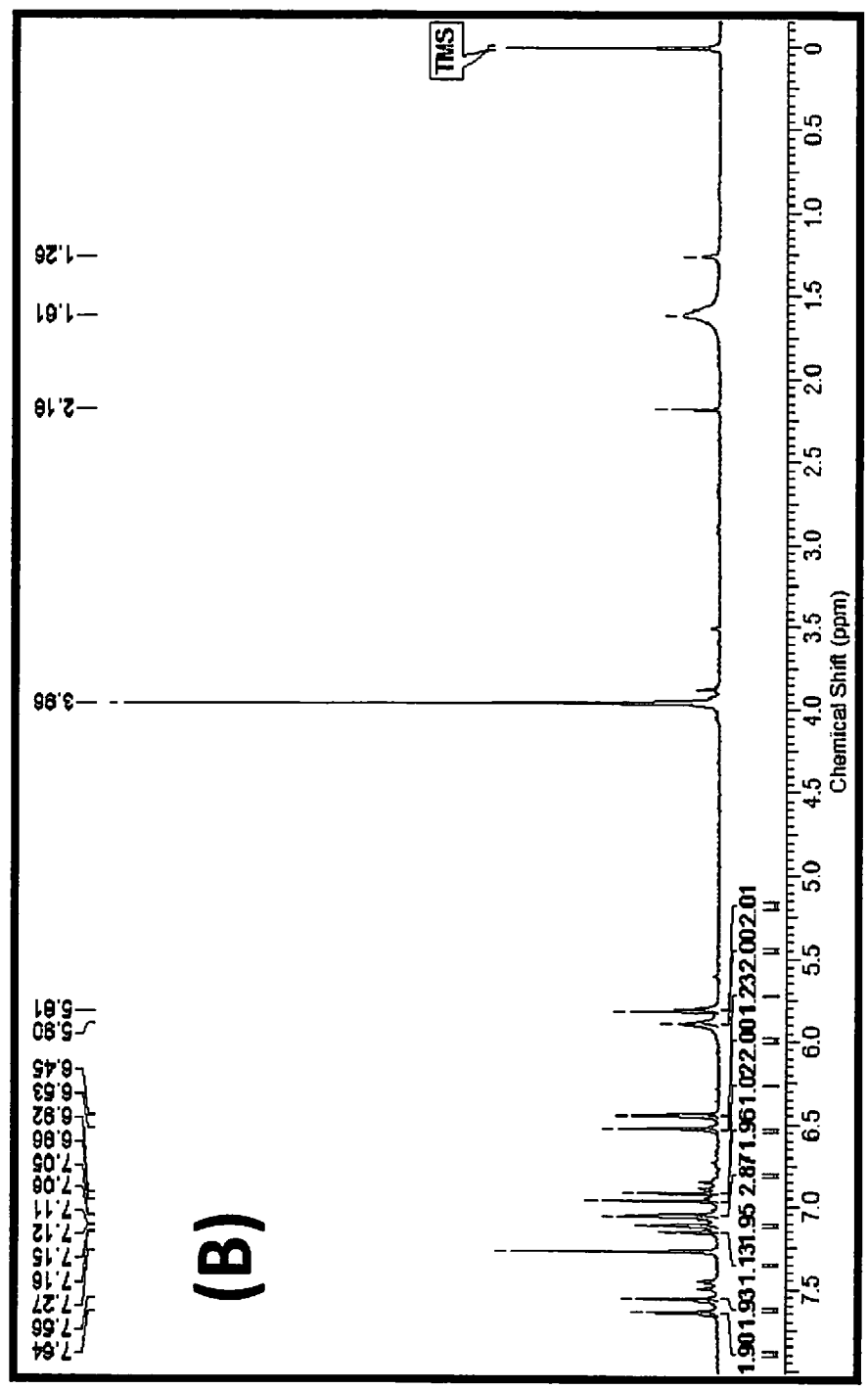

FIG. 9 NMR study of (A) Curcumin and (B) curcumin in SL(A)+ Cur solutions after four month stability.

DETAILED DESCRIPTION OF THE INVENTION

Present invention provides a complex comprising acidic sophorolipid and curcumin ((SL(A)+Cur), wherein, curcumin is solubilized and nano-encapsulated in acidic sophorolipid to improve the water solubility, stability and bioavailability of curcumin in order to enhance its anti-cancer activity.

Further, the present invention provides a pharmaceutical composition comprising acidic sophorolipid and curcumin complex together with one or more pharmaceutical excipients.

In another aspect, the present invention provides a process for preparation of acidic sophorolipid and curcumin complex, wherein the complex is prepared by sonication driven supramolecular self-assembly.

In yet another aspect, the acidic sophorolipid and curcumin complex thus obtained was characterized by using UV-Vis and photoluminescence (PL) spectroscopy, Dynamic Light Scattering (DLS), Zeta potential, Fourier-transform infrared (FTIR), X-ray diffraction (XRD) and Scanning, Transmission electron microscopy (SEM and TEM, respectively).

The present acidic sophorolipid curcumin formulations exhibit a significantly improved intracellular uptake in cancer cells as compared to freely available curcumin. The optimized curcumin formulation also exhibit superior cytotoxicity against cancer cells. Thus, the invention provides a cost effective nano self-assembly for improved curcumin delivery and therapeutic efficacy in cancer treatment.

The present invention provides acidic sophorolipid and curcumin ((SL(A)+Cur) complex, prepared by sonication driven supramolecular self-assembly, wherein, curcumin is solubilized and nano-encapsulated in acidic sophorolipid to improve the water solubility, stability and bioavailability of curcumin in order to enhance its therapeutic activity. The present invention provides a pharmaceutical composition comprising acidic sophorolipid and curcumin complex together with one or more pharmaceutical excipients.

Accordingly, the present invention provides a complex comprising a bio-surfactant and an insoluble molecule. The complex comprises a therapeutic molecule which is generally insoluble in aqueous conditions. The insoluble therapeutic molecule selected in the present invention is curcumin. Acidic sophorolipid, a bio-surfactant is employed in the complete dissolution of the therapeutic molecule and leads to its encapsulation in the acidic sophorolipid shell.

The present complex is determined for its physical characteristics and its biological attributes compared to the curcumin and sophorolipid components when used individually, and curcumin when dissolved in polar solvent.

The sophorolipid component of the present complex is produced from non-pathogenic yeast species (*Candida bombicola*) using fermentation process, wherein oleic acid is used as the substrate. The microbial sources are selected from the group yeast species consisting of *Starmerella bombicola, Candida apicola, Rhodotorula bogoriensis*, and *Wickerhamiella domercqiae*. The organically synthesized sophorolipid obtained in the crude mixture post down streaming process of fermentation is subjected to separation procedures such as extraction, precipitation or distillation, and later purified using chromatographic techniques.

The sophorolipid obtained is acidic, and is most prominently obtained by fermentation of glucose and oleic acid in the presence of *C. bombicola*. Preferably, an acidic sophorolipid is used in the preparation of the present complex.

Further, the curcumin component of the present complex is isolated from the rhizomes of *C. longa* and subjected to further purification procedures. Both of these components are prepared in aqueous solutions.

The present invention provides a complex comprising acidic sophorolipid and curcumin having particle size ranging from 5 to 30 nm.

The acidic sophorolipid and curcumin complex thus obtained was characterized by using UV-Vis and photoluminescence (PL) spectroscopy, Dynamic Light Scattering (DLS), Zeta potential, Fourier-transform infrared (FTIR), X-ray diffraction (XRD) and scanning, Transmission electron microscopy (SEM and TEM, respectively).

The particle size distribution, SEM and TEM analysis indicate the nano-encapsulation of curcumin in acidic sophorolipid, the solubilization of curcumin and its stability in aqueous solutions. The reduced particle size of the present complex demonstrates the decreased agglomeration of curcumin in aqueous solutions due to its capping by sophorolipid.

The present acidic sophorolipid curcumin formulations exhibit a significantly improved intracellular uptake in cancer cells as compared to freely available curcumin. The optimized curcumin formulation also exhibit superior cytotoxicity against cancer cells. Thus, the invention provides a cost effective nano self-assembly for improved curcumin delivery and therapeutic efficacy in cancer treatment.

The present invention provides a complex comprising acidic sophorolipid and curcuminin a ratio preferably ranging from 6:1 to 1:1. More the preferably, the complex comprising acidic sophorolipid and curcumin is in a ratio of 5:1, respectively 16.66% of curcumin encapsulated in 83.33% sophorolipid The present invention provides a pharmaceutical composition comprising acidic sophorolipid and curcumin complex together with one or more pharmaceutical excipients. The excipients are selected from the ones known in the art such as tableting excipients, injectable excipients, and excipients that can be used for preparation of liquids, solutions, suspensions, syrups and accordingly can be formulated as tablets, capsules, pellets, granules, oral and injectable powders and liquids.

Alternatively, the pharmaceutical composition comprises an additional biological agent having anti-oxidant, anti-cancer and anti-adipogenic activity. The agent exhibiting anti-cancer activity may be selected from the group consisting of rituximabbevacizumab, imatinibleuprorelin, lenalidomidecetuximab and trastuzumab.

The present invention provides pharmaceutical compositions comprising acidic sophorolipid and curcumin complex for various forms of administration such as oral, liquid and parenteral.

The invention provides pharmaceutical compositions comprising acidic sophorolipid and curcumin complex and optionally with an additional anticancer agent for the treatment of breast cancer.

The invention provides pharmaceutical compositions comprising acidic sophorolipid and curcumin complex, wherein the amount of the complex will be ranging from 0.001 to 99.99% of the total weight of the formulation.

The invention provides methods of preparing the conventional dosage forms and methods of administrations.

The present invention provides a method of treating breast cancer in a subject, which method comprises administering an effective amount of the pharmaceutical compositions comprising acidic sophorolipid and curcumin complex optionally with one or more pharmaceutical excipients, to a subject in need thereof.

The present invention provides a method of treating breast cancer in a subject, which method comprises administering an effective amount of the pharmaceutical compositions comprising acidic sophorolipid and curcumin complex and optionally with an additional anti-cancer agent, to a subject in need thereof.

Accordingly, the therapeutically effective concentration of the present complex is in the range of 7-14 µg/ml.

The invention provides a complex comprising acidic sophorolipid and curcumin for use in the treatment of cancer, obesity, adipogenesis and in the suppression of fatigue. More preferably, the present acidic sophorolipid and curcumin complex is used in the treatment of and/or in the preparation of medicament for treating breast cancer.

Cyto-toxic effects of the present complex comprising acidic sophorolipid and curcumin on MCF-7 cells (Michigan Cancer Foundation-7 invasive breast ductal carcinoma cells) and MDA-MB-231 (adenocarcinoma) breast cancer cells exhibits enhanced activity compared to curcumin when dissolved in polar solvent and acidic sophorolipid individually. The relative cyto-toxicity of curcumin with its SL (A) complex was extensively superior due to the presence of glucose moiety. The results further suggest that acidic sophorolipid based formulations, which solubilize curcumin in nano-encapsulation after lipid digestion, show great potential for curcumin cell entry.

The invention provides a simple process for preparation of acidic sophorolipid and curcumin complex, wherein the acidic sophorolipid and curcumin complex is prepared by sonication driven supramolecular self-assembly.

The acidic sophorolipid and curcumin complex thus obtained was characterized by using UV-Vis and photoluminescence (PL) spectroscopy, Dynamic Light Scattering (DLS), Zeta potential, Fourier-transform infrared (FTIR), X-ray diffraction and scanning, Transmission electron microscopy (SEM and TEM, respectively).

Figure 2:
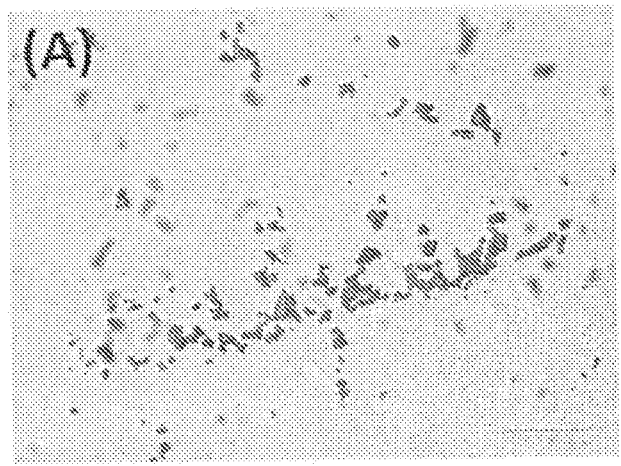
Figure 2:
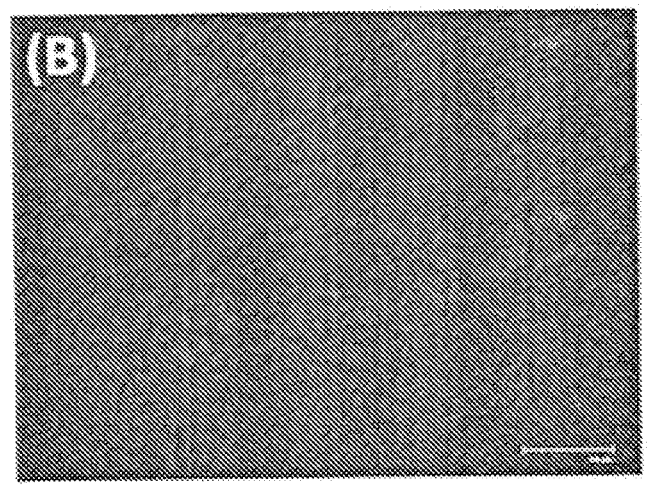
Figure 2:
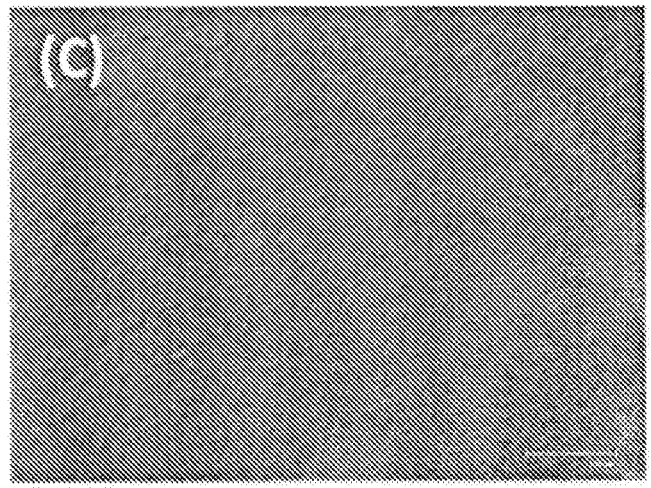
Figure 2:
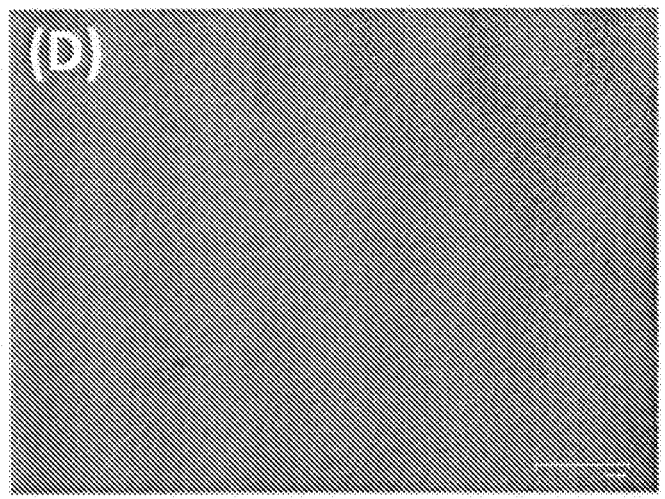

Accordingly, the absorption maxima of the present complex was determined to be 420 nm, this absorption pattern is similar to the absorption maxima of curcumin dissolved in polar solvent, thereby indicating the encapsulation of curcumin in the sophorolipid shell. Further, the present complex exhibits photoluminescence. A large blue shift results when curcumin is bound to the SL(A) micelles. This occurs due since curcumin in SL(A) micelles create a lipophilic condition via binding to the hydrophobic regions. Besides the shift in the fluorescence maximum, there is improvement in the fluorescence intensity of curcumin upon formation of the self-assembly with SL(A) (FIG. 2). XRD data in FIG. 6 indicates that characteristic diffraction peaks present in curcumin are absents in the spectrum of the present complex thereby indicating that the curcumin being nano-encapsulated its peaks are to broadened and the XRD is dominated by the structure of the sophorolipid.

EXAMPLES

Following examples are given by way of illustration and therefore should not be construed to limit the scope of the invention.

Example 1

Synthesis of Acidic Sophorolipid+Curcumin Nano-Assemblies
i. Preparation of Acidic Sophorolipid Solution
   Acidic sophorolipid was produced by fermentation (SSF) of *Candida bombicola* (ATCC22214) from Oleic acid.
ii. Preparation of Curcumin Solution
   Curcumin was purchase from Sigma Aldrich and used as it received. The solvent was allowed to evaporate and curcumin was preserved in distilled water in aqueous conditions at room temperature.
iii. Preparation of SL(A)+Cur Complex
   SL(A) dissolved in 25 ml distilled water (1 mg/ml) was taken in 50 ml beaker, maintained in bath sonication for 15 to 30 minutes. 5 ml Curcumin solution (1 mg/ml) in distilled water was added drop wise during sonication of acidic sophorolipid at the rate of 0.5 ml/min. Final volume was dried by rotavapor followed by addition of 5 ml water for complete dispersion of curcumin to achieve a uniform solution. Solution was filtered through 0.22 m filter paper to ensure that only SL(A)+Cur self-assembly compound would go across the membrane.

Example 2

Characterization of the Acidic Sophorolipid-Curcumin Complex
i. Optical Properties
   Optical properties of the present complex SL(A)+ curcumin complex were determined by UV-Vis and Photoluminescence studies analysis. Accordingly, the optical properties of SL(A), curcumin and the present sophorolipid-curcumin (SL(A)+Cur) self-assembly were compared. UV-Vis absorption spectra were recorded on Varian CARY 100 Bio UV-Vis spectrophotometer respectively, with 10 mm quartz cell at 25±0.1° C. For recording the spectra, 3 ml solutions of SL(A), Cur and SL(A)+Cur solution were prepared with having a concentration of 100 µg/ml. The solutions of this were mixed gently and subsequently the spectra were recorded.

Figure 1:
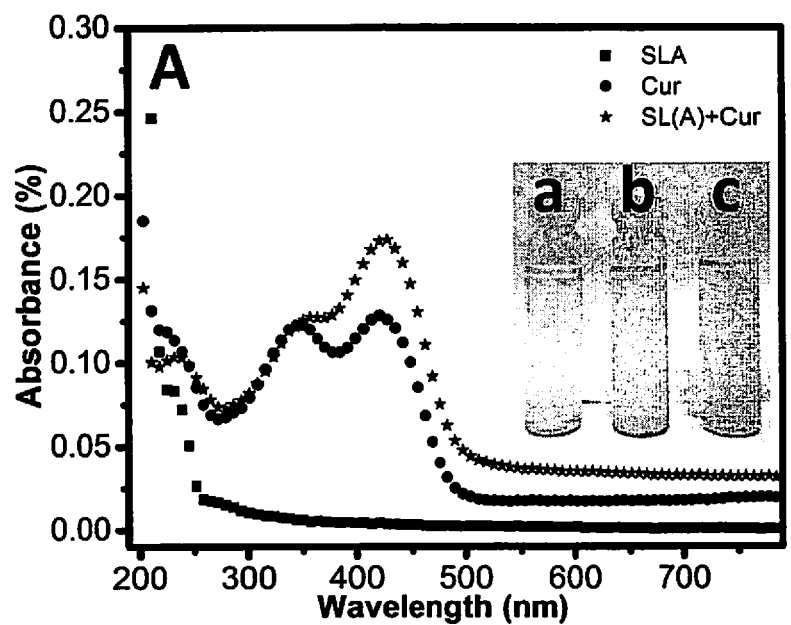
Figure 1:
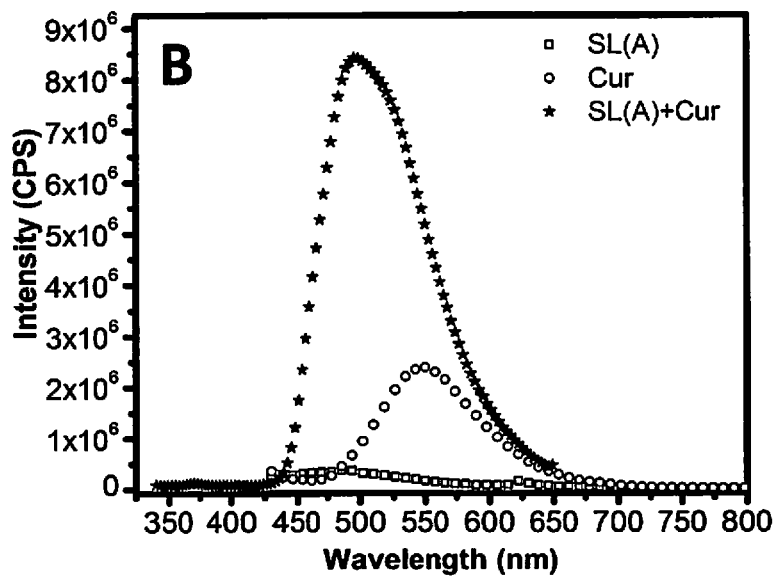
Figure 1:
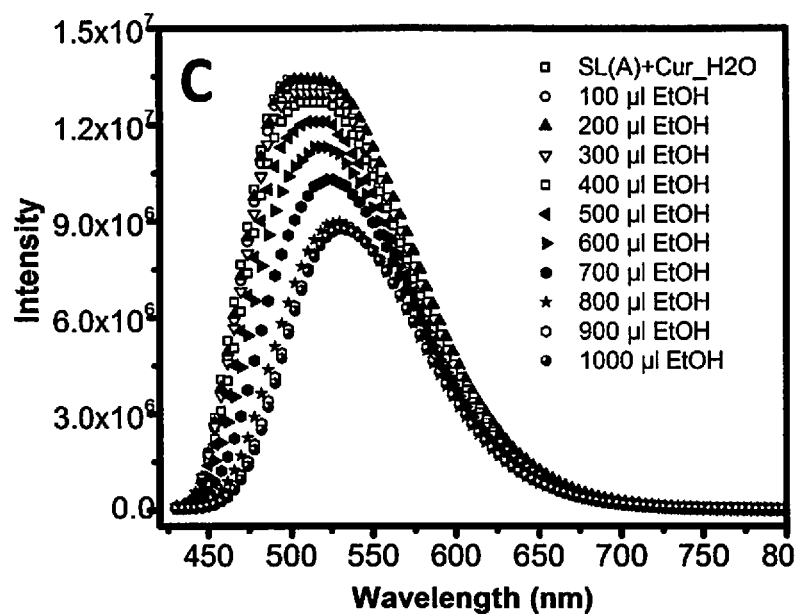
Figure 1:
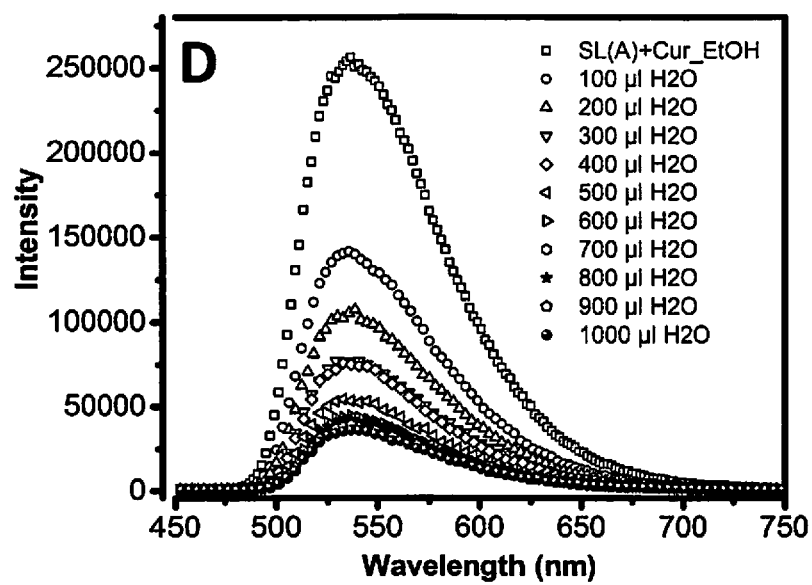

The optical properties of acidic sophorolipid (SL(A)), curcumin (Cur) and the present SL(A)+Cur complex showed significant differences. Visible differences in the appearance of each of the test solutions were observed. The SL(A) solution appeared transparent, curcumin solution appeared to be turbid, whereas SL(A)+Cur solution appeared transparent, however was yellow in color indicating complete curcumin solubilization. Thus, the photo-physical properties of curcumin were very sensitive to the medium. The absorption maximum of curcumin was found to be 420 nm when dissolved in organic solvent. However, its absorbance decreased in aqueous solution due to degradation of curcumin in water by a reaction at the keto-enol group. In the present SL(A)+Cur complex the sophorolipid shell contributed a hydrophobic surface to the curcumin core and the outer hydrophilic portion of the sophorolipid assisted in the solubility of the complex in water (FIG. 1(a)). This assembly in aqueous solution greatly assisted in stabilization of the complex giving rise to enhanced absorption at 420 nm in the aqueous medium. (A. Barik et al, *Photochem and Photobio*, 2003, 77(6), 597-603 and A. Patel et al, *J. Agric. Food Chem.* 1999, 47, 4992-97)

Photoluminescence (PL) of the SL(A), curcumin and SL(A)+Cur samples was recorded for comparison by excitation at the specific wavelength of 420 an in an aqueous solution. SL(A) individually failed to exhibit any photoluminescence, while curcumin exhibited weak excitonic emission at 550 nm due to low solubility. However, on addition of SL(A) in curcumin aqueous solution a strong emission was observed at 500 nm reflecting tremendous enhancement of the fluorescence intensity (FIG. 1(b)). The fluorescence maximum shifted from a broad unremarkable 550 nm band to a remarkable blue shifted band at 500 nm. To confirm the improvement in PL, additional experiments were performed. On addition of ethanol gradually in the present complex photoluminescence quenching is observed. This was postulated to be probably due to disturbance of nonpolar region around curcumin nanoparticles created by the SL(A) self-assembly. Furthermore, a red shift is observed (from 500 nm to 550 nm) with the addition of ethanol to the SL(A)+Cur aqueous solution, clearly indicating a gradual degradation of the self-assembly yielding the original structure itself (FIG. 1(c)).

A large blue shift observed at 500 nm in the absorption maxima indicated that curcumin was bound to the SL(A) micelles thus signifying that curcumin in SL(A) micelles created a nonpolar environment, possibly by binding to the hydrophobic regions of SL(A) micelles. Besides the shift in the fluorescence maximum, there was a remarkable improvement in the fluorescence intensity of curcumin upon formation of the self-assembly with SL(A) (FIG. 2). As seen from FIG. 2(b) a very feeble fluorescence was observed in the case of individual curcumin particulates, while the well-dispersed and well distributed SL(A)+Cur nanoparticulates exhibited enhanced fluorescence (FIG. 2(d)).

ii. DLS Measurements

Figure 3:
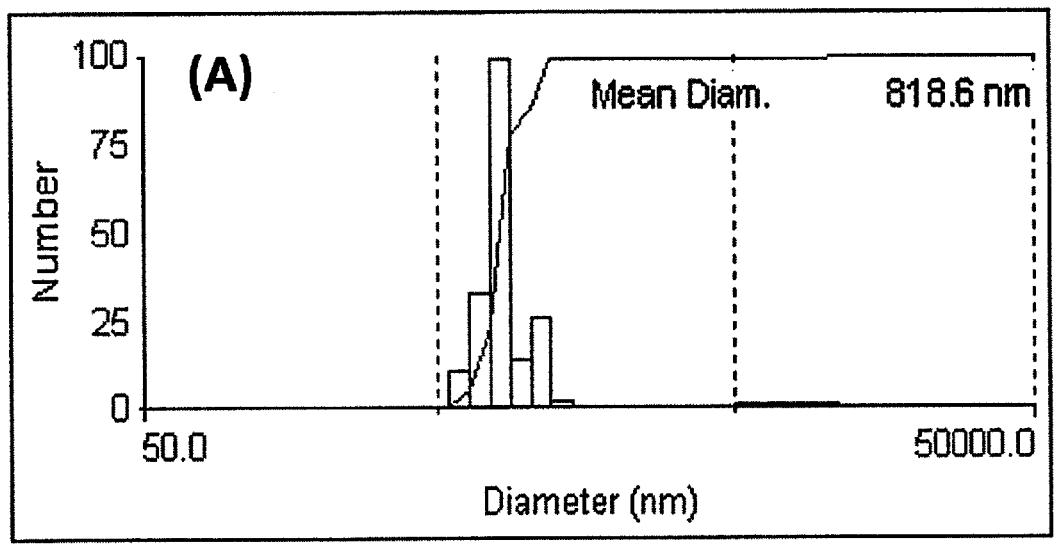
FIG. 3 depicts the Dynamic Light Scattering (DLS) wherein FIG. 3(A) relates to Curcumin showing hydrodynamic radius of 818.6 nm. Further FIG. 3(B) relates to SL(A) with hydrodynamic radius 6.8 nm, FIG. 3(C) SL(A)+Cur with hydrodynamic radius 15.5 nm.
Figure 3:
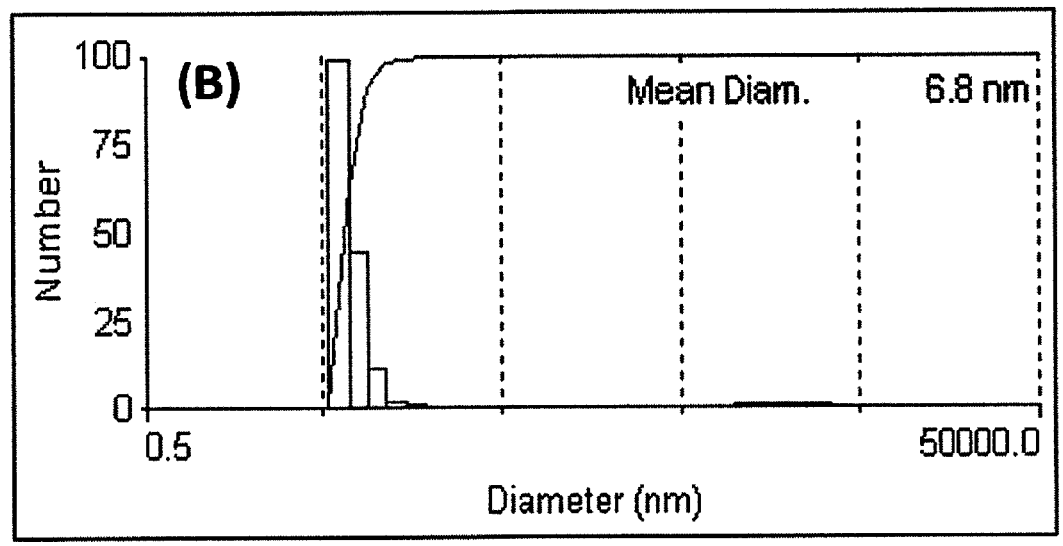
Figure 3:
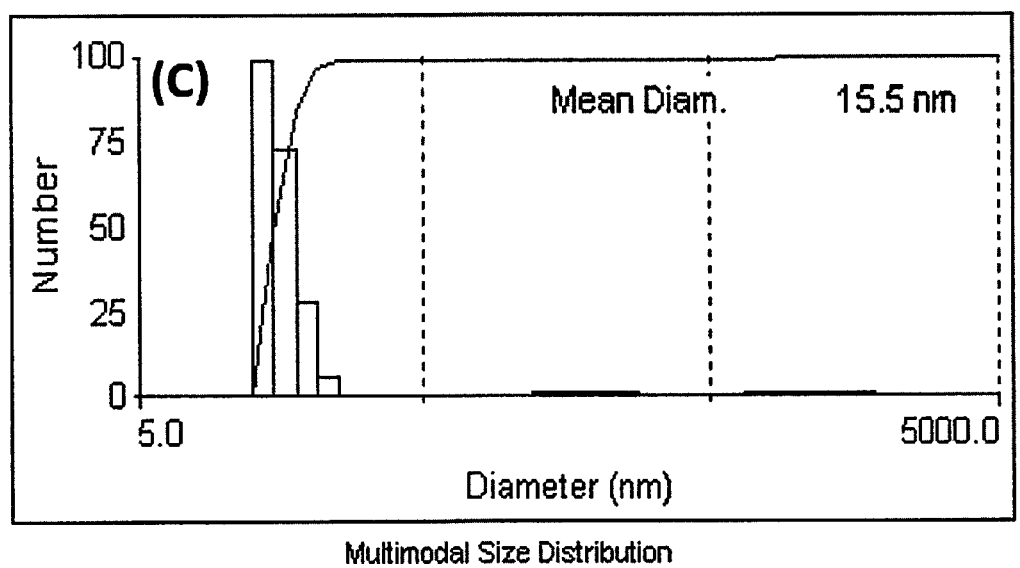

The Dynamic Light Scattering (DLS) measurements were carried using the out on Brookhaven Instrument model 90 Plus Particle Size Analyzer. The solutions, i.e. Cur, SL(A) and the present SL(A)+Curcumin nano-assembly were analyzed at a constant shutter opening diameter in the DLS apparatus. DLS measurements for Cur, SL(A) and SL(A)+Cur (10 mg of each dissolved in 10 ml $H_2O$) exhibited hydrodynamic radii of about 818 nm, 6.8. nm and 15.5 nm, respectively (FIGS. 3 (A), (B) and (C)). This was also confirmed with the results obtained by SEM and TEM analysis depicted in FIG. 4. Field emission scanning electron microscopy images acquired on FEI QUANTA 200 microscope, equipped with a tungsten filament gun, operating at WD 10.6 mm and 20 kV. A 10 μL aliquot of all three sample solution were placed on silicon wafer and fixed on copper stubs with help of carbon tape. The samples were dried at room temperature for overnight and images were recorded without gold coating.

SL(A), Cur and SL(A)+Cur samples were further examined by scanning electron microscopy (FIGS. 4A, B and C). SL(A) exhibited a ribbon type morphology (FIG. 4(a)), Cur appeared as large chunks forming undefined structures (FIG. 4(b)), whereas SL(A)+Cur showed fibrous morphology (FIG. 4(c)) which differed distinctly from that of SL(A).

It may be noted that the morphologies of the structures in the solutions evolve in the solution drying process and do not represent the situation in the solution, it is therefore clear that morphological organization of SL around Cur with hydrophilic groups protruding outside would change their organization and therefore the morphology during the drying process as compared to SL(A) itself which does not have such preferential molecular organization in the solution. The TEM images at different levels of magnification (FIGS. 4 (d), (e) and (f)) apparent in SEM (FIG. 4(c)) due to the corresponding limited resolution show tiny fairly uniformly dispersed Cur nanoparticles (<about 20 nm, some agglomerated on TEM grid) which were not apparent in SEM (FIG. 4(c)) due to the corresponding limited resolution.

These results are reflective of the size of the SL(A)+Cur particles to be in the range of 5 to 30 nm indicating that there is a decreased agglomeration of curcumin in aqueous solution due to its capping by SL(A) and there is a definite increase in the size of SL(A)+Cur complex as compared to only SL(A) because of the additional encapsulation of cur nanoparticles.

iii. Zeta Potential

The surface charges of the SL(A), Cur and SL(A)+Cur were determined using a zeta potential analyzer (Brookhaven Instruments Corporation, NY). The average zeta potentials of the nano self-assembly dispersions were determined without any dilution.

Figure 4:
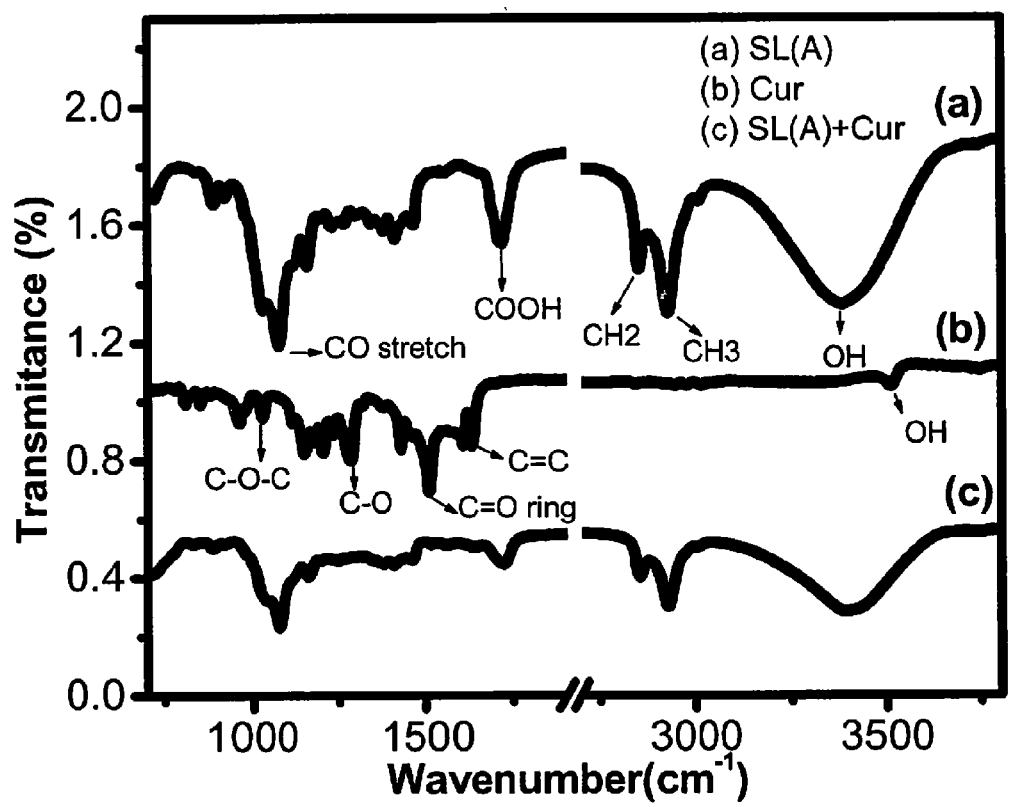
FIG. 4 depicts SEM images of SL(A) showing ribbon like structures in FIG. 4(a) and SEM images of Cur as undefined structure in FIG. 4(b), and FIG. 4(c) relate to TEM analysis for high resolution images of the present SL(A)+Cur nano-assembly showing Curcumin as nanoparticles encapsulated in SL(A) structure (scale bar 0.5, 10, 0.5 and 0.1 μm respectively).

To comprehend the stability of the present complex, zeta potential measurements were performed on all the samples. The zeta potential values for the three sample were SL(A)=−17.30 mV, Cur=−15.14 mV, SL(A)+Cur=−24.38 mV (FIG. 4 B, D, F respectively).

The increase in the zeta potential of SL(A)+Cur compared to individual SL(A) and cur was taken as an indication of the increased stability of the self-assembled complex.

iv. Stability of SL(A)-Cur Complex

The stability of the nano-complex in aqueous environment over a period of four months was confirmed by UV/Vis spectra, PL (FIG. 8) UV-Visible spectra of SL (A), Curcumin and SL(A)+Cur solutions. SL(A) solution shows absorbance at λ=234 nm and Curcumin solution at λ=344 and 420 nm while SL(A)+Cur showing increase absorption at one peak at 420 nm. Blue line shows the stability of nano complex after four months. NMR study of (A) Curcumin and (B) curcumin in SL(A)+Cur solutions after four month stability (FIG. 9).

v. FTIR Analysis

FTIR spectra were recorded with KBr pellets on FTIR spectroscopy in transmission mode using a Nicolet Magna IR-750 spectrophotometer at 4 $cm^{-1}$ resolution with 64 scans between 4000 and 400 $cm^{-1}$. Two milligram of dried powder was mixed with 198 milligram KBr and analyze by instrument.

Figure 5:
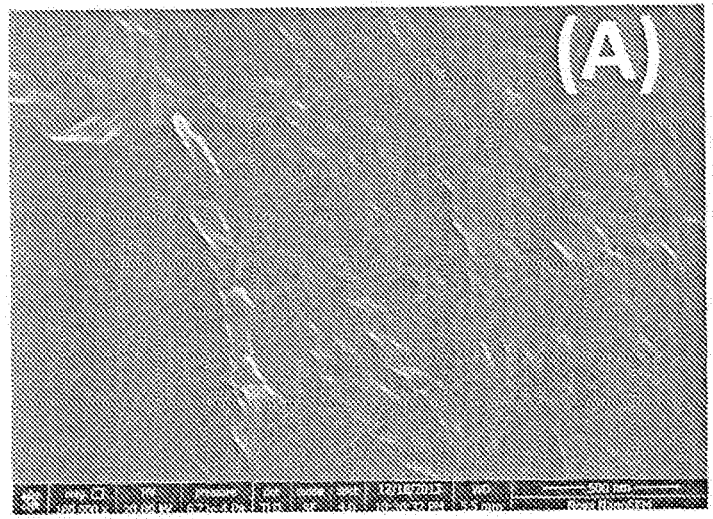
FIG. 5 depicts FTIR analysis of SL(A), Cur and SL(A)+Cur, the presentSL(A)+Cur complex spectra exhibits all the peaks related to the SL(A) compound which indicate the encapsulation of curcumin in side self assembly of ribbon type structure in water.
Figure 5:
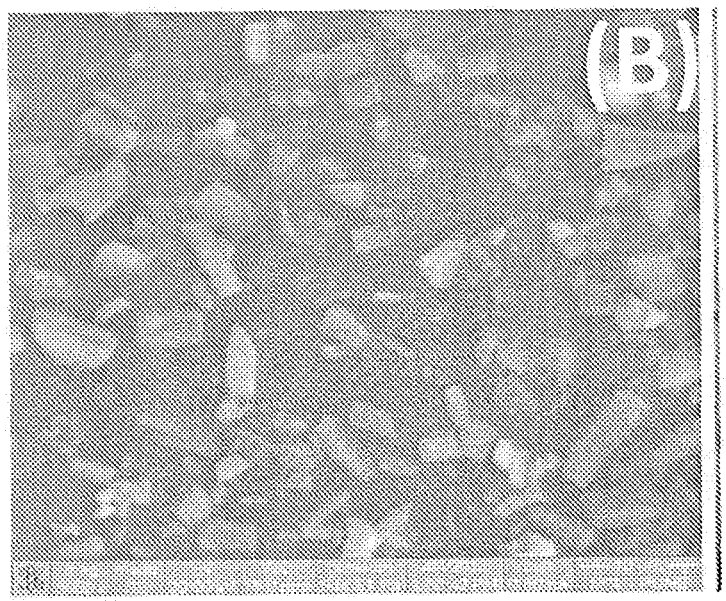
Figure 5:
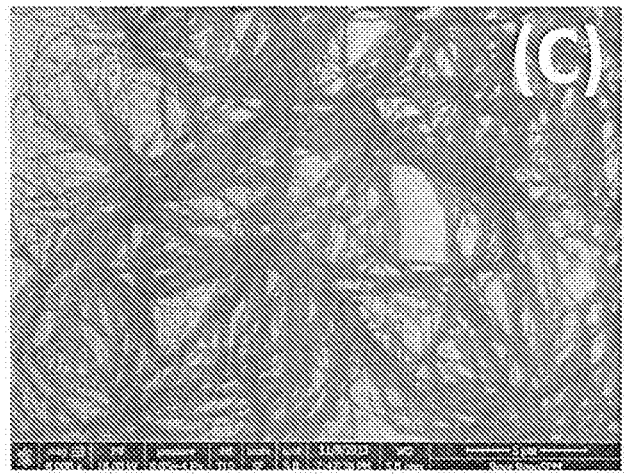
Figure 5:
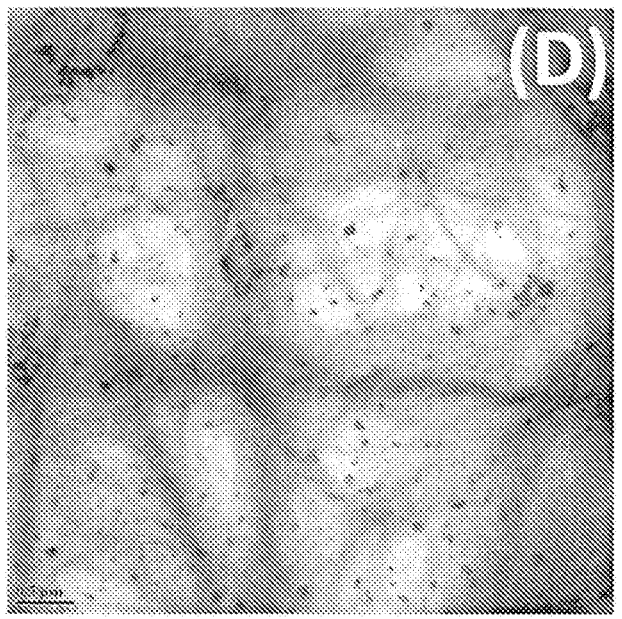
Figure 5:
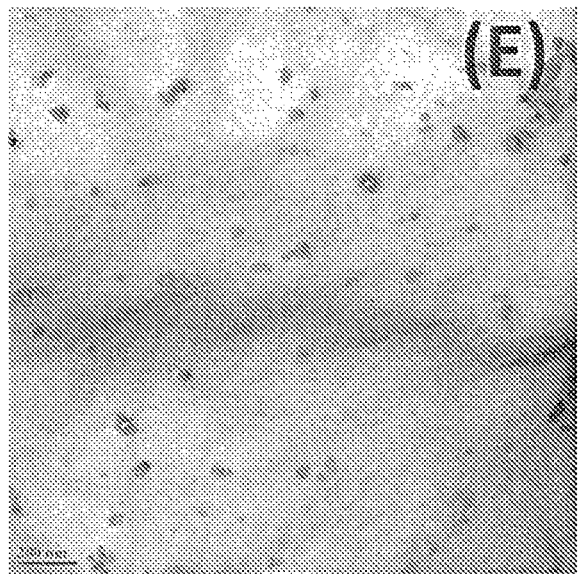
Figure 5:
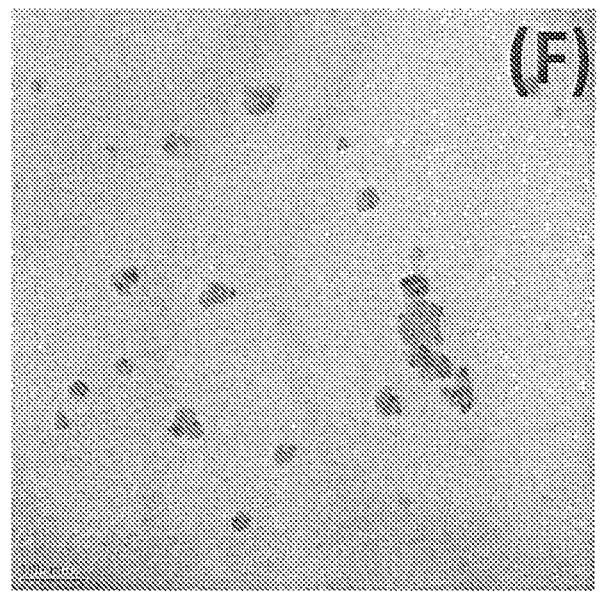

FTIR spectra for the SL(A), Cur and SL(A)+Cur after sonication treatment for 30 minutes is indicated in FIG. 5. The SL(A) reveals a broad band at 3350 $cm^{-1}$ corresponding to the OH stretch frequency in the glucose moiety of the molecule. The asymmetrical and symmetrical stretch modes of methylene ($CH_2$) groups occur at 2928 and 2854 $cm^{-1}$, respectively. SL(A) has two strong absorption bands arising from C—O and C—O stretching; the C—O absorption band at 1,744 $cm^{-1}$ may include contributions from these groups. Moreover, sugar C—O stretch of C—O—H groups is found at 1,048 $cm^{-1}$ and the band at 1,452 $cm^{-1}$ corresponds to the C—O—H in-plane bending of carboxylic acid (—COOH) in the structure of the product. All these structural details are in conformity with the literature reports. (P. Singh, and S. S. Cameotra, *TRENDS in Biotechnology*, 2004, 22, 142)

The FTIR spectrum of Cur was shown as a sharp one peak at 3508 cm$^{-1}$ thereby indicating the presence of OH. The strong peak at 1626 cm$^{-1}$ has a predominantly mixed (C=C) and (C=O) character. Another strong band at 1601 cm$^{-1}$ was attributed to the symmetric aromatic ring stretching vibrations (C=C ring). The 1508 cm$^{-1}$ peak is assigned to the (C=O), while enol C=O peak was obtained at 1272 cm$^{-1}$, C—O—C peak at 1023 cm$^{-1}$, benzoate trans-CH vibration at 959 cm$^{-1}$ and cis CH vibration of aromatic ring at 713 cm$^{-1}$. (D. Patra et al *Photochem and Photobio*, 2012, 88, 319).

The FTIR spectrum of SL(A)+Cur showed all peaks relating to SL(A) and Cur peaks are observed to have been suppressed due to nano-encapsulation.

vi. X-Ray Diffraction (XRD) Analysis

To examine the crystallinity of micelle-encapsulated SL(A)+Cur, XRD analysis was performed. XRD analysis of samples (FIG. 6) was done over broad angle range (2θ values, 10-80 degrees).

The powder X-ray diffractograms of SL(A), Cur and SL(A)+Cur dried powders are shown in FIG. 6. The characteristic peaks of curcumin appeared at 2θ values at 7.96, 8.90, 12.26, 14.54, 17.24 implied the presence of curcumin in crystalline form. It was found that the characteristic diffraction peaks of curcumin were absent in the spectrum of the SL(A)+Cur nano-encapsulation which suggested that curcumin being nano-encapsulated its peaks are too broadened and the XRD pattern in dominated by the structure of sophorolipid component.

Interestingly, the diffraction patterns of the material obtained after dissolution in chloroform showed a pattern similar to that of pure curcumin, indicating that the complex is broken down and the encapsulated curcumin is released.

vii. Statistical Analysis

All the experiments were performed in triplicates and repeated twice and the data has been presented as mean±SD. Statistical analysis was conducted with the Graph Pad 4 prism program using one-way ANOVA. The p values used for comparisons were <0.05. IC$_{50}$ values were calculated using Kyplot software.

The cytotoxic potential of aqueous SL(A)+Cur was tested by MTT assay in breast cancer cell lines, MCF-7 and MDA-MB-231 and was compared with that of aqueous SL(A) and Cur dissolved in ethanol. After treatment with SL(A), both the breast cancer cell lines exhibited 80-100% viability up to the concentration of 160 µg/ml showing that the SL(A) were almost non-toxic. On the other hand, both Curcumin and SL(A)+Curcumin decreased the viability of breast cancer cells in a dose-dependent manner. Beyond 40 µg/ml dose, SL(A)+Curcumin showed slightly more toxicity in both MCF-7 and MDA-MB-231 cells compared to Curcumin. These results indicate that sophorolipids increase the bioavailability of Curcumin in aqueous medium without affecting its anticancer potential.

Example 3

Determination of Bioavailability of Curcumin
Cyto-Toxicity Assay

In order to determine whether acidic sophorolipid enhanced the bioavailability of Curcumin in cancerous cell lines, the cytotoxic potential of the aqueous SL(A)+Cur complex was tested in breast cancer lines MCF-7 and MDA-MB-231 and was compared with that of aqueous SL(A), Cur in water, and Cur dissolved in ethanol, the latter was used as a positive control.

Materials Employed

Tissue culture plasticware was purchased from BD Biosciences, CA, USA. Cur, Dulbecco's Modified Eagles Medium (DMEM), Fetal Bovine Serum (FBS) and 3-(4,5-dimethylthiazol-2-yl)-2,5-diphenylthiazolium bromide (MTT) were obtained from Sigma-Aldrich (St. Louis, Mo.). Penicillin/streptomycin and L-glutamine were obtained from Gibco BRL, CA, USA.

Cyto-toxicity analysis of the present curcumin-SL(A) complex was performed using mammalian breast cancer cell lines by the MTT dye uptake assay. Accordingly, cells were treated with concentrations of the aforesaid solution differing in the range of 0-160 µg/ml of SL(A), Curcumin dissolved in ethanol and SL(A)+Cur. MTT solution (5 mg/ml) was added to each well and the cells were cultured for another 4 h at 37° C. in a 5% CO$_2$ incubator. The formazan crystals formed were dissolved by addition of 90 µL of SDS-DMF (20% SDS in 50% DMF). After 15 min, the concentration of colored formazan derivative was determined by measuring optical density (OD) using the ELISA microplate reader (Biorad, Hercules, Calif.) at 570 nm (OD: 570-630 nm). The percentage viability was calculated as:

% Viability=[OD of treated cells/OD of control cells]×100

Percentage Viability Observed Post Treatment

After treatment with the solution containing acidic sophorolipids i.e. SL(A), both the cancer cell lines exhibited 80-100% viability up to concentrations of 160 µg/ml indicating its non-toxicity to the cells. It was pertinently noted that the present SL(A)+Cur nano-complex exhibited enhanced activity, indicating the presence of acidic sophorolipid increasing the bioavailability of curcumin, hence the present complex exhibits anticancer activity at extremely low doses commencing from concentrations as low as 6.66 µg/ml compared to a higher dose concentration of 40 µg/ml of curcumin dissolved in ethanol to inhibit growth of MCF-7 cells (FIG. 7(a)).

However, it may be noted in the case of MCF-7 cells, that Cur dissolved in ethanol was more toxic than the present nano-complexes specifically at moderate and low concentrations. In the low to moderate dose range (5-20 µg/ml), Cur dissolved in ethanol has more concentration compared to the concentration of Cur present in the SL(A)+Cur nano-complexes (0.83-3.33 µg/ml). Thus, the nano-complexes do not show effective inhibition within this concentration. However, at higher dose range (40-160 µg/ml), the concentration of Cur in SL(A)+Cur was also increased (10-30 µg/ml) and thus an increase in cytotoxicity was observed.

Likewise, in MDAMB-231 cells (FIG. 7(b)), SL(A)+Cur exhibited cytotoxicity at 3.33 µg/ml compared to 20 µg/ml concentration of Cur dissolved in ethanol. Cur dissolved in water exhibited no activity against the cancerous cell lines, due to the insolubility of Cur in water. These results clearly show that the bioavailability of Cur was increased in SL(A)+Cur complex as compared to that of Cur dissolved in ethanol.

More importantly, MCF-7 showed increased susceptibility to anticancer drugs at lower doses compared to MDAMB-231, the reason being the difference in estrogen and progesterone (ER/PR) receptor status in the cell lines. MCF-7 is ER/PR positive while MDAMB-231 is ER/PR negative, thereby being slightly insensitive to lower concentrations of anticancer drugs. Moreover, SL(A) makes the Cur present in the NPs more bio-available at lower doses as compared to higher doses of curcumin dissolved in ethanol which explains the increased cytotoxicity of nano-complex. This improved cytotoxicity of SL(A)+Cur complexes compared to Cur in ethanol in cancer cell lines was interpreted to be due to tautomeric molecular form of curcumin after SL(A) encapsulation.

TABLE 1

Anticancer activity of SL(A), Cur And SL(A) + Cur in tabulated amount For Cancer Cell Lines MCF-7

| Amount (µg/ml) | SL(A) (% viability) | Cur (% viability) | SL(A) + Cur (% viability) |
|---|---|---|---|
| 0 | 100 | 100 | 100 |
| 5 | 100 | 100 | 100 |
| 10 | 100 | 100 | 90 |
| 20 | 97 | 100 | 75 |
| 40 | 95 | 95 | 10 |
| 80 | 90 | 93 | 0 |
| 120 | 80 | 91 | 0 |

TABLE 2

Anticancer activity of SL(A), Cur And SL(A) + Cur in tabulated amount For Cancer Cell Lines MDAMB 231

| Amount (µg/ml) | SL(A) (% viability) | Cur (% viability) | SL(A) + Cur (% viability) |
|---|---|---|---|
| 0 | 100 | 100 | 100 |
| 5 | 95 | 100 | 98 |
| 10 | 90 | 100 | 90 |
| 20 | 85 | 100 | 48 |
| 40 | 82 | 95 | 12 |
| 80 | 80 | 93 | 5 |
| 120 | 80 | 91 | 0 |

Example 4

Preparation of Composition Comprising Bioavailable Curcumin

The present acidic sophorolipid curcumin based nano-emulsion was formulated into tablet dosage form by wet granulation method. The amount of granulating liquid added was optimized as it affects the granules and tablet characteristic. The moisture content evaluation is a very critical parameter which was estimated to be in the range of 1-3% in order to produce a qualified tablet.

ADVANTAGES OF THE INVENTION

Co-sonication of curcumin and acidic sophorolipid in aqueous solution leads to a dramatic enhancement of curcumin bioavailability through size reduction and encapsulation. The solubilization of curcumin by nano-encapsulation is an effective aspect of designing drug delivery systems.

Sophorolipid as an environmentally friendly, biocompatible and very important class of biosurfactants which has been complexed with Curcumin to increase its solubility, stability, fluorescence and bioavailability.

It is further established through the present invention that the complex formation of Curcumin with SL (A) increases the cellular uptake possibility of Curcumin by a large degree. Particles size distribution, TEM and zeta potential analysis clearly explain its increased cellular uptake by nano-encapsulation and stability in aqueous solution.

We claim:

1. A curcumin-sophorolipid complex comprising acidic sophorolipid and curcumin in a ratio ranging from 6:1 to 1:1 (w/v).

2. The complex according to claim 1, wherein the curcumin is solubilized and encapsulated in the acidic sophorolipid to improve solubility, stability, and bioavailability of the curcumin.

3. The complex according to claim 1, wherein said complex comprises sophorolipid and curcumin in a ratio of 5:1.

4. The complex according to claim 1, wherein said complex has a particle size ranging from 5 to 30 nm.

5. The complex according to claim 1, wherein said complex is in aqueous form.

6. The complex according to claim 1 for use in treatment of breast cancer.

7. The complex according to claim 1 for use in preparation of medicament for treatment of breast cancer.

8. A process for the preparation of curcumin-sophorolipid complex according to claim 1, wherein said process comprises the steps of:
   (i) sonicating 80 to 90 (wt %) sophorolipid solution for a period ranging from 15 to 30minutes with addition of 10 to 20 (wt %) curcumin solution at a rate of 0.5 ml/min to obtain a solution; and
   (ii) drying the solution of step (i) followed by addition of water for complete dispersion of curcumin to achieve a uniform dispersion;
   (iii) filtering the uniform dispersion of step (ii) to obtain the curcumin-sophorolipid complex.

9. A pharmaceutical composition comprising curcumin-sophorolipid complex according to claim 1 and a pharmaceutically acceptable excipient, wherein the curcumin-sophorolipid complex ranges from 0.001 to 99.99% of total weight of the pharmaceutical composition.

10. The pharmaceutical composition according to claim 9, wherein the composition comprises an agent having anti-oxidant, anti-cancer, or anti-adipogenic activity.

11. The pharmaceutical composition according to claim 9, wherein the excipient is selected from the group consisting of tableting excipients, injectable excipients, and excipients for liquid dosage forms.

12. The pharmaceutical composition according to claim 9, wherein the composition is formulated as a tablet, capsule, pellet, granule, oral powder, injectable powder,syrup, solution, liquid ampoule, dispersion, aerosol spray, semi-solid, softgel, aerosol, or suspension.

13. The pharmaceutical composition according to claim 10, wherein the agent is selected from the group consisting of rituximab, bevacizumab, imatinib, leuprorelin, lenalidomidecetuximab, and trastuzumab.

14. A method of treating breast cancer in a subject, wherein the method comprises administering to a subject having breast cancer a therapeutically effective amount of the pharmaceutical composition according to claim 9.

15. A method of treating breast cancer in a subject, wherein the method comprises administering to a subject having breast cancer a therapeutically effective amount of the pharmaceutical composition according to claim 10.

* * * * *